United States Patent [19]

Haken et al.

[11] Patent Number: 4,600,712
[45] Date of Patent: Jul. 15, 1986

[54] FUNGICIDALLY ACTIVE COMPOSITIONS CONTAINING ETHENE DERIVATIVES

[75] Inventors: Pieter T. Haken, Eastling, Nr. Faversham; Shirley B. Webb, Faversham, both of England

[73] Assignee: Shell Oil Company, Houston, Tex.

[21] Appl. No.: 785,693

[22] Filed: Oct. 9, 1985

Related U.S. Application Data

[63] Continuation-in-part of Ser. No. 535,496, Sep. 26, 1983, abandoned.

[30] Foreign Application Priority Data

Sep. 27, 1982 [GB] United Kingdom ............. 8227480

[51] Int. Cl.⁴ .............. A01N 43/54; A01N 43/58; A01N 43/60; A01N 55/02
[52] U.S. Cl. .................... 514/188; 514/184; 514/247; 514/255; 514/256; 514/277; 514/357
[58] Field of Search ............. 514/188, 184, 247, 255, 514/256, 277, 357

[56] References Cited

U.S. PATENT DOCUMENTS

| | | | |
|---|---|---|---|
| 3,157,663 | 11/1964 | Bencze | 260/294.9 |
| 3,196,158 | 7/1965 | Bencze | 260/294.9 |
| 3,337,565 | 8/1967 | Bencze et al. | 544/224 |
| 3,337,568 | 8/1967 | Bencze et al. | 544/224 |
| 3,361,863 | 1/1967 | Villani | 260/293 |
| 3,370,063 | 2/1968 | Suh | 260/294 |
| 3,846,553 | 11/1974 | Shen et al. | 514/345 |
| 3,928,352 | 12/1975 | Taylor | 544/336 |
| 4,428,948 | 1/1984 | Miller et al. | 514/183 |

OTHER PUBLICATIONS

Erdtman et al, Acta Chemica Scandinavica 22 (1968) 1475-1481.
Buu-Hoi et al, Journal of the Chemical Society (C), (1969), pp. 2069-2070.
Afridi et al., Journal of the Chemical Society (London) Perkin Transactions I, (1976) pp. 315-320.
Clarke et al., J. Org. Chem. 27, 553-556 (1962).
Walker, J. Med. Chem. 8, 583-588 (1965).
Castle et al., J. Org. Chem. 20, 987-989 (1955).
Galiazzo, vol. 64 (1966) 17532-3.

*Primary Examiner*—Allen J. Robinson

[57] ABSTRACT

Certain species of fungi are controlled by ethene derivatives of the formula:

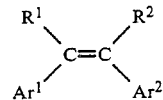

wherein one of Ar¹ and Ar² is one of certain N-heterocyclic moieties and the other is halogen-substituted phenyl, R¹ is hydrogen or alkyl and R² is —CN or —C-(O)XR, wherein X is oxygen or sulfur and R¹ has a defined meaning.

2 Claims, No Drawings

FUNGICIDALLY ACTIVE COMPOSITIONS CONTAINING ETHENE DERIVATIVES

This application is a continuation-in-part of application Ser. No. 535,496, filed on Sept. 26, 1983, now abandoned.

DESCRIPTION OF THE INVENTION

The present invention relates to fungicidally active compositions containing ethene derivatives, to novel ethene derivatives, to a process for their preparation and to a method of controlling fungal growth using the compounds and compositions.

J. Org. Chem. 20 987-9, and J. Med. Chem. 8 583-8, disclose that certain ethene derivatives may be used as intermediates in the preparation of compounds which are physiologically active. J. Org. Chem. 27 553-6 identifies further similar ethene derivates. There is no suggestion that these compounds have any use in agriculture. It has now been unexpectedly found that certain ethane derivatives of this chemical type exhibit valuable fungicidal activity.

The present invention therefore provides a fungicidal composition which comprises a carrier and, as active ingredient, a compound of the general formula $$AR^1R^1C=CAr^2R^2 \tag{I}$$

or an N-oxide, salt or metal salt complex thereof, wherein one of $Ar^1$ and $Ar^2$ represents unsubstituted pyridyl, pyrazinyl, pyridazinyl or pyrimidinyl group, and the other of $Ar^1$ and $Ar^2$ represents a halogen-substituted phenyl group; $R^1$ represents a hydrogen atom or an alkyl group; and $R^2$ represents a cyano group, a —COOH group or an ester or thioester thereof.

Throughout this specification, unless otherwise stated, any aliphatic moiety present preferably contains up to 6, especially up to 4, carbon atoms.

As stated above, the invention includes compositions containing metal salt complexes and salts of compounds of formula I. Suitable salts include salts with sulphonic acids, for example benzene- or toluenesulphonic acid, carboxylic acids for example tartaric or acetic acid, or inorganic acids for example the hydrohalic acids or sulphuric acid. If $R^2$ represents a —COOH group, a salt may be a metal salt, for example and alkali or alkaline earth metal salt, the ammonium salt, or a substituted ammonium salt, for example an alkyl-substituted ammonium salt, for example an alkyl-substituted ammonium salt. Suitable metal salts which form complexes with compounds of formula I include these of heavy metals such as iron, copper, zinc and manganese, in which the anions may, for example, be derived from one of those acids given above.

The compounds of formula I exist as geometric isomers. Optical isomers may be present, the number of possibilities for isomerism depending on the specific groups present. Formula I should be understood to include all individual isomers and mixtures thereof.

Preferred compounds of formula I and N-oxides, salts and complexes thereof, are those in which one of $Ar^1$ and $Ar^2$ represents an unsubstituted pyrazine or, especially, an unsubstituted pyridyl group and the other of $Ar^1$ and $Ar^2$ represents a mono- or dihalophenyl group; more preferably one of $Ar^1$ and $Ar^2$ is an unsubstituted 3-pyridyl group and the other of $Ar^1$ and $Ar^2$ is a mono- or dichloro or fluoro substituted phenyl group, preferably a dichloro substituted phenyl group.

Preferably $R^1$ represents a methyl group or, especially, a hydrogen atom.

If $R^2$ represents an ester or thioester of —COOH, this ester or thioester is derived from an alkanol or alkanethiol having up to 6 carbon atoms.

The invention further provides a process for the preparation of a novel compound according to the invention which comprises reacting a compound of the formula

with a compound of the formula

wherein $Ar^1$, $Ar^2$, $R^1$ and $R^2$ have the meanings given in formula I; and if desired, converting the resulting compound of the invention into any other compound of the invention.

In general, the process according to the invention may lead to a mixture of geometric isomers of formula I. When $R^2$ represents a cyano group the predominant isomer formed is usually that in which $Ar^1$ and $Ar^2$ are trans, whereas when $R^2$ is other than cyano the corresponding cis isomer usually predominates. The exact ratio of products produced depends of course on the precise reaction conditions, and may also depend upon the substituents present in the reactants.

The molar ratio of the reactants is not critical and may for example be in the range of from 5:1 to 1:5, especially 2:1 to 1:2. It is often convenient to use approximately stoichiometric ratios.

The reaction is suitably carried out in the presence of a solvent; typical solvents include, for example, alcohols such as methanol or ethanol; ethers such as dimethoxyethane or tetrahydrofuran; chlorinated hydrocarbons such as methylene chloride; anhydrides such as acetic anhydride; esters such as ethyl acetate; amides such as dimethyl formamide or dimethyl acetamide; ketones such as acetone, dimethyl ketone and methyl ether ketone; and nitroalkanes such as nitromethane.

The reaction is preferably carried out in the presence of a base. Suitable bases include primary, secondary or tertiary amines, for example, triethylamine or piperidine; alkali metal hydrides, amides or alkoxides, for example, sodium ethoxide; or alkali metal or alkaline earth metal hydroxides, for example, potassium hydroxide. The reaction temperature is suitably in the range of from 0° to 180° C. It may in some cases be convenient to carry out the reaction at the reflux temperature of the reaction mixture.

Compounds of formulae II and III may be prepared by methods analogous to methods known in the art.

As stated above, a resulting compound of the invention may, if desired, be converted into any other compound of the invention. Such reactions may be carried out by methods analogous to methods known in the art. For example, a compound in which $R^2$ represents a cyano group may be hydrolysed or alcoholised to give the appropriate acid or ester. A compound in which $R^2$ represents a —COOH group may be converted into an ester or thioester by reaction with the appropriate alcohol or thiol.

A compound of formula I may be converted into a salt or a metal salt complex thereof by methods analogous to known methods, for example by reaction with an oxidizing agent or with the appropriate acid, base or salt. A resulting salt can be converted into the free compound by reaction with an acid binding agent or an acid, as appropriate.

The invention further provides a method of controlling fungus at a locus, which comprises applying to the locus a compound or a composition according to the invention. Suitable dosages are, for example, in the rage of from 0.05 to 4 kg active material per hectare. The method of the invention is especially useful for the treatment or prevention of fungal attack in seeds, soil or plants; crops susceptible to powdery mildews, for example cereals or apples, may be treated.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used. Preferably compositions according to the invention contain 0.5 to 95% by weight of active ingredient.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples or suitable liquid carriers are water, alcohols such as ispropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as keorsene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25 to 75% by weight of active compound and usually contain, in addition to the solid carrier, 3–10% by weight of a dispersing agent, 2–15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sendimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or (up to 95%) more by weight of finely divided active material, 3–7% by weight of a blend of surfactants, which act as wetting, dispersing, suspending and binding agents, and may contain up to 3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.5% by weight to as much as about 95% by weight of a compound of Formula I as the active ingredient.

The compositions of the invention may also contain other ingredients, for example, other compounds possessing pesticidal, especially insecticidal, acaricidal, herbicidal or fungicidal properties, as are appropriate to the intended purpose.

Protection of a locus or area from undesirable plants is effected by applying a compound of Formula I, ordinarily in a composition of one of the aforementioned types, to soil in which the seeds of the unwanted plants are present, or to the foliage of the unwanted plants. The active compound, of course, is applied in an amount sufficient to exert the desired action.

The amount of the compound of the invention to be used in combatting undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kg per hectare of the compund of Formula I will be satisfactory.

EXAMPLES SHOWING PREPARATION OF FUNGICIDES OF THE INVENTION

The following Examples illustrate the invention. The terms "cis" and "trans" are used to indicate the relationship of $Ar^1$ and $Ar^2$ about the double bond.

EXAMPLE 1

Preparation of 2-(2,4-dichlorophenyl)-3-(3-pyridyl)propenoic acid (cis isomer) (1)

A mixture of pyridine-3-aldehyde (21.4 g), 2,4-dichlorophenylacetic acid (40.1 g), triethylamine (20 ml) and acetic anhydride (160 ml) was stirred and heated under reflux for 5 hours while maintaining a temperature of 150° C. After cooling, the reaction mixture was diluted with water (150 ml) and left to stand overnight. The crystalline solid that had separated was filtered off, washed thoroughly with water and dried. After recrystallization from ethanol (600 ml) 1 was obtained as pale yellow crystals; melting point 208–211° C.; yield 71%. The following elemental analysis results were obtained:

Calculated: C: 57.14; H: 3.06; N: 4.76; Found: C: 57.1; H: 3.2; N: 4.7.

EXAMPLE 2

Preparation of n-butyl 2-(2,4-dichlorophenyl)-3-(3)-pyridyl)-propenoic acid ester (cis isomer) (2)

A mixture of 1 (32.1 g) and thionyl chloride (150 ml) was stirred and heated under reflux for 3 hours. Excess thionyl chloride was removed in vacuo and the residue triturated with dry diethyl ether. 2-(2,4-dichlorophenyl)-3-(3-pyridyl)-propenoyl chloride hydrochloride (cis isomer) (2A) was filtered off, washed with diethyl ether and dried in a vacuum oven. The yield of product was 82%. The following elemental analysis results were obtained:

Calculated: C: 48.14; H: 2.58; N: 4.01; Found: C: 47.8; H: 2.6; N: 4.0.

Sodium (0.9 g) was dissolved in a dry n-butanol (70 ml) under nitrogen, and the resultant solution added to a stirred suspension of 2A (6.8 g) in dry dimethoxyethane. The mixture was stirred and heated under reflux for 16 hours. After cooling, the mixture was filtered and the solvent evaporated from the filtrate under reduced pressure. The residue was taken up in methylene chloride, washed three times with water and dried using magnesium sulphate.

After filtration and removal of the solvent in vacuo, the residual oil was subjected to column chromatography on silica gel, eluting with diethyl ether/hexane (2:1), to give 2, in 75% yield as a pale yellow oil.

The following elemental analysis results were obtained:

Calculated: C: 61.71; H: 4.86; N: 4.00; Found: C: 62.2; H: 5.1; N: 3.9.

EXAMPLE 3

Preparation of (1-methylpropyl) 2-(2,4-dichlorophenyl)-3-(3-pyridyl)-thiolo-propenoic acid ester (cis isomer) (3)

A stirred suspension 2A (6.35 g) in dry dimethoxyethane (50 ml) under nitrogen was treated with dry triethylamine (1.85 g). A suspension of the sodium salt of 1-methylpropane-1-thiol (0.0182 mole) in the dry dimethoxyethane (25 ml) was then added, and the mixture was filtered and solvent recovered from the filtrate in vacuo. The residual oil was taken up in diethyl ether, washed three times with water and dried using magnesium sulphate. After filtration and removal of the solvent, the residual oil was subjected to column chromatography on silica gel, eluting with diethyl ether/hexane (2:1). 3 was thus obtained in 52% yield as a pale yellow oil.

The following elemental analysis results were obtained:

Calculated: C: 59.02; H: 4.64; N: 3.83; Found: C: 58.5; H: 4.7; N: 3.8.

EXAMPLE 4

Preparation of 1-cyano-1-(4-chlorophenyl)-2-(3-pyridyl)ethene (trans isomer) (4)

A solution of 4-chlorobenzyl cyanide (7.58 g) and pyridine-3-aldehyde (5.35 g) in absolute ethanol (50 ml) was warmed to 50° C.; 3.5 ml of a solution of sodium (2.74 g) in absolute ethanol (32 ml) was added and the mixture was left without further heating. After 1 hour, the solid product was filtered off, washed with ethanol, and then diethylether, and dried. Recrystallization of this material from ethanol (150 ml) with charcoal treatment gave 4 in 48% yield as pale yellow needles; m.p. 141°–143° C.

The following elemental analysis results were obtained:

Calculated: C: 69.85; H: 3.74; N: 11.64; Found: C: 69.9; H: 3.7; N: 11.6.

EXAMPLE 5

Preparation of the copper (II) chloride complex of the compound of Example 4

To a stirred solution of 4 (2.4 g) in warm ethanol (50 ml) was added a solution of copper (II) chloride (0.6725 g) in ethanol (15 ml). After ½ hour the pale blue green copper (II) chloride complex (2 moles of ethene derivative per mole of $CuCl_2$) was filtered off, washed with ethanol, then diethylether, and dried. The yield was 89%, m.p. 290°–292° C. (decomposition).

Elemental Analysis: Calculated: C: 54.59; H: 2.92; N: 9.1; Found: C: 53.8; H: 2.7; N: 9.0.

EXAMPLES 6 to 29

By methods analogous to those described in Examples 1 to 5, the following compounds were prepared.

Analysis and physical data figures where available are given in Table I.

calculated to give an application rate of 1 kg/ha. After drying, the petioles of the sprayed leaves are dipped in water and the leaves returned to high humidity for a further 96 hours incubation, followed by assessment. Assessment is based on the percentage of the leaf area covered by sporulation compared with that on control

TABLE I

| Example No. (cis/trans isomer) | Ar$^1$ | Ar$^2$ | R$^1$ | R$^2$ | Physical Data |
|---|---|---|---|---|---|
| 6 (cis) | 2,4-dichlorophenyl | 3-pyridyl | H | COOH | M.p.: 262–264° C. |
| 7 (trans) | 4-F—phenyl | 3-pyridyl | H | CN | M.p.: 145–147° C. |
| 8 (trans) | 4-Cl—phenyl | 3-pyridyl | H | CN | M.p.: 112–114° C. |
| 9 (trans) | 3-pyridyl | 2,4-dichlorophenyl | H | CN | M.p.: 114–116° C. |
| 10 (cis) | 3-pyridyl | 4-Cl—phenyl | H | COOH | M.p.: 221–224° C. |
| 11 (cis) | 2,4-dichlorophenyl | 3-pyridyl | H | 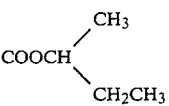 | oil |
| 12 (cis) | 2,4-dichlorophenyl | 3-pyridyl | H | COSC(CH$_3$)$_3$ | M.p.: 87–89° C. |
| 13 (cis) | 2,4-dichlorophenyl | 3-pyridyl | H | COOCH$_3$ | oil |
| 14 (cis) | 2,4-dichlorophenyl | 3-pyridyl | H | COO(CH$_2$)$_3$CH$_3$ | oil |
| 15 (trans) | 3-pyridyl | 2,4-dichlorophenyl | H | COOCH$_3$ | oil |
| 16 (cis) | 2,4-dichlorophenyl | 3-pyridyl | H | COOCH$_2$CH$_3$ | M.p.: 64–68° C. |
| 17 (cis) | 3-pyridyl | 2,4-dichlorophenyl | H | COOCH$_3$ | M.p.: 41–47° C. |
| 18 (cis) | 3-pyridyl | 2,4-dichlorophenyl | H | 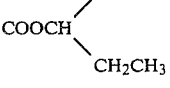 | oil |
| 19 (cis) | 3-pyridyl | 2,4-dichlorophenyl | H | 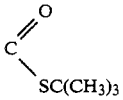 | oil |
| 20 (cis) copper (II) chloride complex (2 moles pyridine compound per mole CuCl$_2$) | 3-pyridyl | 2,4-dichlorophenyl | H | COOCH$_3$ | M.p.: 176–178° C. (decomposition) |
| 21 (trans) | 3-pyridyl | 2,4-Cl$_2$—phenyl | CN | H | M.p.: 148–151° C. |
| 22 (cis) | 3-pyridyl | 2,4-Cl$_2$—phenyl | CN | CH$_3$ | |
| 23 (trans) | 3-pyridyl | 2,4-Cl$_2$—phenyl | CN | CH$_3$ | M.p.: 131–133° C. |
| 24 (trans) | 3-pyridyl | 2,4-Cl$_2$—phenyl | COOH | H | M.p.: 185–190° C. |
| 25 (cis) CuCl$_2$ complex | 3-pyridyl | 2,4-Cl$_2$—phenyl | COOCH$_3$ | H | M.p.: 162–164° C. |
| 26 (cis) | 3-pyridyl | 2,4-Cl$_2$—phenyl | H | CN | M.p.: 66–67.5° C. |
| 27 (trans) CuCl$_2$ complex | 3-pyridyl | 2,4-Cl$_2$—phenyl | CN | H | M.p.: 305–307° C. |
| 28 (trans) MnCl$_2$ complex | 3-pyridyl | 2,4-Cl$_2$—phenyl | CN | CH$_3$ | M.p.: 242–244° C. |
| 29 (cis) MnCl$_2$ complex | 3-pyridyl | 2,4-Cl$_2$—phenyl | CN | CH$_3$ | M.p.: 245–248° C. |

EXAMPLE 30 EXAMPLES SHOWING ACTIVITY OF FUNGICIDES OF THE INVENTION (a) Activity against vine downy mildew (*Plasmopara viticola*; P.v.a.)

The test is a direct antisporulant one using a foliar spray. The lower surfaces of leaves of whole vine plants are inoculated by spraying with an aqueous suspension containing 10$^5$ zoosporangia/ml 2 days prior to treatment with the test compound. The inoculated plants are kept for 24 hours in a high humidity compartment, and then 24 hours at glasshouse ambient temperature and humidity. The plants are then dried and infected leaves detached and sprayed on the lower surfaces with a solution of active material in 1:1 water/acetone containing 0.04 Triton X-155 (Trade Mark). The spraying is carried out with a moving track sprayer which delivers 620 l/ha, and the concentration of active material is calculated to give an application rate of 1 kg/ha. After drying, the petioles of the sprayed leaves are dipped in water and the leaves returned to high humidity for a further 96 hours incubation, followed by assessment. Assessment is based on the percentage of the leaf area covered by sporulation compared with that on control leaves.

(b) Activity against vine downy mildew (*Plasmopara viticola*; P.v.t.)

The test is a translaminar protectant one using a foliar spray. The upper surfaces of leaves of whole vine plants are sprayed at a dosage of 1 kilogram of active material per hectare using a track sprayer. The lower surfaces of the leaves are then inoculated, up to 6 hours after treatment with the test compound, by spraying with an aqueous suspension containing 10$^5$ zoosporangia/ml. The inoculated plants are kept for 24 hours in a high humidity compartment, 4 days at glasshouse ambient temperature and humidity, and then returned for a further 24 hours to high humidity. Assessment is based on the percentage of leaf area covered by sporulation compared with that on control leaves.

(c) Activity against vine grey mold (*Botrytis cinerea*; B.c.)

The test is a direct eradicant one using a foliar spray. The under-surface of the detached vine leaves are inoculated by pipetting ten large drops of an aqueous suspension containing $5 \times 10^5$ conidia/ml on to them. The inoculated leaves are kept uncovered overnight during which time the fungus has penetrated the leaf and a visible necrotic lesion may be apparent where the drop was made. The infected regions are sprayed directly with a dosage of 1 kg of active material per hectare using a track sprayer as described under (a). When the spray has dried the leaves are covered with a petri dish and the disease allowed to develop under these humid conditions. The extent of the necrotic lesion beyond the original drop together with the degree of sporulation is compared with that on control leaves.

(d) Activity against potato late blight (*Phytophtora infestans*; P.i.p.)

The test measures the direct protectant activity of compounds applied as a foliar spray. Tomato plants, cultivar Ailsa Craig, 1–15 cms high, in monopots are used. The whole plant is sprayed at a dosage of 1 kilogram of active material per hectare using a track sprayer. The plant is then inoculated up to 6 hours after treatment with the test compound, by spraying with an aqueous suspension containing $5 \times 10^3$ zoosporangia/ml. The inoculated plants are kept in high humidity for 3 days. Assessment is based on comparison between the levels of disease on the treated and control plants.

(e) Activity against barley powdery mildew (*Erysiphe graminis*; E.g.)

The test measures the direct antisporulant activity of compounds applied as a foliar spray. For each compound about 40 barley seedlings are grown to the one-leaf stage in a plastic pot of sterile potting compost. Inoculation is effected by dusting the leaves with conidia of *Erysiphe graminis*, spp. hordei. 24 hours after inoculation the seedlings are sprayed with a solution of the compound in a mixture of acetone (50%), surfactant (0.04%) and water using a track sprayer as described under (a). The rate of application is equivalent to 1 kg of active material per hectare. First assessment of disease is made 5 days after treatment, when the overall level of sporulation on the treated plants is compared with that on control plants.

(f) Activity against apple powdery mildew (*Podsophaera leucotrica*; P.l.)

The test is a direct anti-sporulant one using a foliar spray. The upper surfaces of leaves of whole apple seedlings are inoculated by spraying with an aqueous suspension containing $10^5$ conidia/ml 2 days prior to treatment with the test compound. The inoculated plants are immediately dried and kept at glass house ambient temperatures and humidity prior to treatment. The plants are sprayed at a dosage of 1 kilogram of active material per hectare using a track sprayer. After drying the plants are returned to a compartment at ambient temperature and humidity for up to 9 days, followed by assessment. Assessment is based on the percentage of the leaf area covered by sporulation compared with that on leaves of control plants.

(g) Activity against peanut leaf spot (*Cercospora arachidicola*; Ca)

The test is a direct eradicant one using a foliar spray. The upper surfaces of the leaves of peanut plants (12–20 cms high, monopots) are inoculated by spraying with an aqueous suspension containing $10^5$ conidia/ml 4 hours prior to treatment with the test compound. The inoculated plants are kept at high humidity and then allowed to dry before treatment by spraying at a dosage of 1 kg of active material per hectare using a track sprayer. After spraying the plants are moved to a humid compartment at 25°–28° C. for a further period of up to 10 days. Assessment is based on a comparison between the levels of disease on the treated and control plants.

The extent of disease control achieved in these tests is expressed as a control rating in Table II below; greater than 80% disease control is given the rating 2 after the test; control of between 50 and 80% is given the rating 1 after the test.

TABLE II

| Compound of Example No. | Greater than 50% disease control achieved in the below indicated tests | | | |
|---|---|---|---|---|
| 1 | Pvt (2) | Pl (2) | | |
| 2 | Pva (1) | Eg (2) | Pl (2) | |
| 3 | Eg (2) | Pl (2) | | |
| 4 | Pva (1) | Eg (2) | Pl (2) | |
| 5 | Pip (2) | Eg (2) | | |
| 6 | Eg (1) | | | |
| 7 | Pip (1) | | | |
| 8 | Pvt (2) | Bc (2) | Pip (1) | Eg (1) |
| 9 | Eg (2) | Pl (2) | | |
| 10 | Eg (2) | | | |
| 11 | Pvt (1) | Eg (2) | | |
| 12 | Eg (2) | Pr (1) | Ca (1) | |
| 13 | Eg (2) | | | |
| 14 | PiP (1) | Eg (2) | | |
| 15 | Bc (2) | Pip (1) | Eg (2) | |
| 16 | Eg (2) | | | |
| 17 | Pl (2) | Ca (2) | | |
| 18 | Pva (1) | Eg (2) | Pl (2) | |
| 19 | Eg (2) | Pl (2) | | |
| 20 | Pip (1) | Eg (2) | Pl (2) | |
| 21 | Pip (1) | Eg (1) | Pl (1) | |
| 22 | Eg (2) | Pl (2) | | |
| 23 | Eg (2) | Pl (2) | | |
| 24 | Pl (2) | | | |
| 25 | PiP (1) | Eg (1) | Pl (2) | |
| 26 | Eg (2) | Pl (2) | | |
| 27 | Bc (1) | Pip (1) | Eg (1) | |
| 28 | Pl (2) | | | |
| 29 | Eg (2) | | | |

I claim:
1. A method of controlling fungi selected from *Plasmopara viticola*, *Botrytis cinerea*, *Phytophthera infestans*, *Erysiphe graminis*, *Podsophaera leucotrica* or *Cercospora arachidicola*, at a locus which comprises applying to the locus a fungicidally effective amount of a compound of the formula:

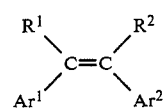

wherein one of $Ar^1$ and $Ar^2$ is selected from the group consisting of pyridyl, pyrazinyl, pyridazinyl and pyrimidinyl, and the other is phenyl substituted by one or two halogen atoms, $R^1$ is hydrogen or alkyl of from one to six carbon atoms, $R^2$ is cyano or —C(O)—X—R wherein X is oxygen (—O—) or sulfur (—S—), with the provisos that when X is oxygen, R is hydrogen or alkyl of from one to six carbon atoms, and when X is sulfur, R is alkyl of one to six carbon atoms, or a salt thereof with an acid selected from the group consisting of sulfonic acids, carboxylic acids, hydrohalic acids and sulfuric acid, and when R is hydrogen, a complex thereof with a salt selected from the group consisting of salts of alkali metals, alkaline earth metals, iron, copper, zinc, manganese, ammonium salts and alkyl-substituted ammonium salts.

2. A method according to claim 1 wherein $Ar^1$ is pyridyl, $R^1$ is hydrogen or methyl, and $R^2$ is —C(O)XR.

* * * * *